United States Patent [19]

Pomot et al.

[11] 4,080,439

[45] Mar. 21, 1978

[54] STARCH COATED ANTIPERSPIRANT DERIVATIVE OF ALUMINUM, PROCESS FOR ITS PREPARATION AND ANTIPERSPIRANT COMPOSITION CONTAINING THE SAME

[75] Inventors: Jean Pomot, Mouans Sartoux; Jean-Philippe Chalaye, Maisons-Alfort, both of France

[73] Assignee: L'Oreal, Paris, France

[21] Appl. No.: 615,091

[22] Filed: Sep. 19, 1975

Related U.S. Application Data

[63] Continuation-in-part of Ser. No. 438,945, Feb. 1, 1974, abandoned.

[30] Foreign Application Priority Data

Feb. 5, 1973  Luxembourg ............................ 66960

[51] Int. Cl.$^2$ ............................................. A61K 9/62
[52] U.S. Cl. ......................................... 424/35; 424/46
[58] Field of Search ....................... 424/47, 68, 32, 35, 424/46

[56] References Cited

U.S. PATENT DOCUMENTS

| | | | |
|---|---|---|---|
| 3,300,387 | 1/1967 | Kole | 424/68 X |
| 3,637,657 | 1/1972 | Morii et al. | 424/180 X |
| 3,664,963 | 5/1972 | Pasin | 424/32 X |
| 3,691,271 | 9/1972 | Charle et al. | 424/47 X |

FOREIGN PATENT DOCUMENTS

| | | | |
|---|---|---|---|
| 368,458 | 3/1932 | United Kingdom | 424/68 |
| 903,407 | 8/1962 | United Kingdom | 424/68 |

*Primary Examiner*—Dale R. Ore
*Attorney, Agent, or Firm*—Cushman, Darby & Cushman

[57] ABSTRACT

An antiperspirant agent having a delayed antiperspirant activity comprises microcrystals of an antiperspirant derivative of aluminum coated with starch partially degraded by acid hydrolysis and having a Stormer viscosity between 60–70. The starch comprises 30–40 weight percent amylose and 60–70 weight percent amylopectin. The antiperspirant agent is present in the composition in amounts of about 2–8 weight percent thereof. The composition can be packaged as an aerosol.

16 Claims, No Drawings

STARCH COATED ANTIPERSPIRANT DERIVATIVE OF ALUMINUM, PROCESS FOR ITS PREPARATION AND ANTIPERSPIRANT COMPOSITION CONTAINING THE SAME

This application is a continuation-in-part of our application Ser. No. 438,945, filed Feb. 1, 1974, now abandoned.

The present invention relates to a new product usefully employed, principally, as a delay-action antiperspirant agent, to a process of producing this product, and to an antiperspirant composition, packaged in the form of an aerosol, which contains this product.

For many years, the use of antiperspirant compositions packaged in the form of an aerosol, has gained wide acceptance. Such antiperspirant compositions are generally composed of an antiperspirant derivative of aluminum such as, for example, micronized basic aluminum hydrochloride suspended in the aerosol propellant, and a perfume dissolved in the propellant, i.e., the continuous phase of the aerosol composition. Further it has been known to include in these compositions such adjuvants as bactericides which function as deodorants, emollients, suspension agents to promote or enhance homogeneity of the composition and thereby facilitate its passage through the distribution valve of the aerosol container.

However, conventional type antiperspirant compositions packaged in the form of an aerosol, exhibit a certain number of significant disadvantages. For instance, because of their great solubility in water, conventional micronized antiperspirant derivatives of aluminum, when applied to the skin, dissolve essentially instantly and completely on contact with perspiration. Consequently their antiperspirant activity is essentially immediate, but disadvantageously of only short duration.

Thus the antiperspirant effect is dissipated rapidly which often requires the user to make several repeated applications of the antiperspirant composition throughout the day.

In an effort to overcome this drawback, manufacturers have at times resorted to including in such compositions antiperspirant derivatives of aluminum in quantities greater than is in fact necessary to control perspiration.

However, after application to the skin, the microcrystals of the aluminum derivative when in direct contact with the perspiration, produce, locally, very concentrated solutions which often cause irritations to users having sensitive skin.

Another disadvantage of conventional aerosol type antiperspirants, which contain both microcrystals of antiperspirant derivatives of aluminum, in suspension in the propellant, and a perfume in solution in the latter, is that frequently a chemical reaction takes place between these two components, with the result that the perfume is often destroyed or changed, especially during storage of the packaged aerosol composition. Consequently, certain perfumes which are particularly sensitive to this type of destructive action cannot be used even though their use is particularly desirable.

Further, because of the irritant effect of antiperspirant derivatives of aluminum, certain disadvantages have been noted among those required to handle significant quantities of these materials, particularly during the production and packaging of antiperspirant compositions in the form of conventional aerosols.

It has now been discovered that the above disadvantages can be avoided by using as the antiperspirant agent is aerosol composition, not a micronized antiperspirant derivative of aluminum in the free state, but rather particles of a hygroscopic antiperspirant derivative of aluminum having a coating of a polymer whose rate of solubilization in water at human body temperature is such that the liberation of the antiperspirant derivative of aluminum is controllably delayed, i.e., it provides a progressive liberation of the antiperspirant derivative during contact with perspiration. Moreover, when the product according to the present invention is employed in aerosol compositions, the antiperspirant derivative of aluminum is isolated from the other components of the aerosol which are in solution or in suspension in the propellant.

To obtain the desired effects, the particles of the coated microcrystals of the antiperspirant derivative of aluminum must possess certain chemical and physical properties. First, it is necessary that the coating material exhibit essentially no reactivity with the antiperspirant derivative of aluminum, which is generally not the case for a majority of polymers and especially for certain natural polymers, such as polypeptides or gums such as gum arabic. It is also necessary that polymer coating exhibit sufficiently slow swelling and dissolution characteristics in water or in perspiration at human body temperature so as to liberate only progressively the antiperspirant derivative of aluminum coated therewith. Moreover, when the coated antiperspirant derivative of aluminum is employed in an aerosol, it is necessary that the polymer coating material be completely insoluble and not swell up in the propellant, the latter generally comprising a mixture of fluoronated hydrocarbons such as those known under the trademark "FREON", and that it be impermeable to the propellant so that no other component in solution in the propellant, and notably the perfume, can come into contact with the antiperspirant derivative of aluminum, during storage in the aerosol container.

In addition to these requirements, it is preferable that the polymer coating material exhibit some cosmetic properties itself, and especially be a softener for the skin.

Materials capable of satisfying these requirements and which, moreover, are insoluble in alcohol, are certain types of starch degraded by acid hydrolysis.

It is well known that there is often used in industry starches which are not in their raw or original state but rather starches which have been modified and principally starches modified by controlled acid hydrolysis to alter their viscosity. These modifications by controlled acid hydrolysis are described in the literature, for example, by Davidson and Sittig, "Water-Soluble Resin", Reinhold Book Corp. 2nd Ed. pages 30 and following.

Thus, the present invention has for an object a new industrial product usefully employed as an antiperspirant agent having a delayed action, comprising microcrystals of an antiperspirant derivative of aluminum coated by a starch partially degraded by acid hydrolysis and having a Stormer viscosity ranging between 60–70, preferably about 65, said starch containing 30–40 weight percent amylose fraction, and 60–70 weight percent amylopectin fraction, the said antiperspirant derivative of aluminum being a basic aluminum halide such as basic aluminum hydrochloride and basic aluminum hydrobromide.

The starch employed in the present invention is a starch rich in amylose, i.e., having straight chains which are only slightly subjected to being hydrated, contrary to ordinary starches which are rich in amylopectin, i.e., having branched chains which are easily hydrated. This starch is partially degraded, by acid hydrolysis, for example, under pressure in hydrochloric acid, to the desired viscosity. The viscosity, which can be measured with a Stormer drum viscosimeter, ranges between 60–70 and preferably about 65. In a particularly advantageous manner, the product according to the invention can be obtained with a cornstarch having an amylose content of 35%, such as that commercially available under the mark "HI-SET" by National Starch Company. The product of the present invention has the property of exhibiting a considerable delay to hydration when it is placed in the presence of water at a temperature lower than 50° C.

In order to facilitate its use in aerosols, the product of the present invention can advantageously be produced in the form of a powder, consisting of finely divided particles having a diameter between 10–50 microns, and preferably between 20–30 microns. This dimension is particularly favorable to the passage through the distribution valve of the aerosol container and lends itself advantageously to good adherence of the particles to the skin.

The present invention also relates to a process for obtaining the product defined above, the said process comprising introducing into a current of air at an elevated temperature, generated for example in an atomizer drier, an aqueous gel of the starch defined above containing an antiperspirant derivative of aluminum. The aqueous gel of degraded starch can be obtained by producing a suspension of starch in cold water; heating this suspension, with agitation to a temperature between 80°–90° C and preferably to about 85° C so as to impart fluidity to the gel; and then adding thereto the antiperspirant derivative of aluminum, either in the form of crystals, or in the form of an aqueous solution of conventional concentration, for example a 30 to 55% solution of basic aluminum hydrochloride. The gel thus obtained is maintained at a temperature between 80°–90° C during its introduction into the atomizer drier. The temperature of the air at the inlet to the atomizer drier, which can be of conventional design, can be maintained between 200°–230° C, and the exit temperature can be maintained for example at 110°–120° C.

The concentration of the antiperspirant derivative of aluminum employed in the starch gel can be determined by the weight ratio of the antiperspirant derivative of aluminum to starch (dry basis) that is desired in the final product. Conveniently, this weight ratio is advantageously between 1:10 and 1:1.

The concentration of degraded starch in the aqueous gel ranges between about 5–30 and, preferably between 10–15, weight percent thereof.

Further, the weight ratio of the antiperspirant derivative of aluminum to degraded starch influences the rate of liberation of the antiperspirant derivative of aluminum in perspiration, this being all the more slow as this ratio is low.

In order to compare the rate of solubilization of the coated antiperspirant derivative of aluminum as a funcrion of the weight ratio of the antiperspirant derivative of aluminum to starch (dry basis), in the product according to the invention, the following laboratory test was conducted.

For this test there were employed particles coated in accordance with the invention containing a constant weight $p$ of the antiperspirant derivative of aluminum. A constant volume of slightly agitated water, maintained at a temperature of 37° C and having a pH of 6 at the beginning of the test was also employed using a conventional conductivity meter. The maximum conductivity of a solution formed by total solubilization of weight $p$ of the antiperspirant derivative of aluminum in the constant volume of water defined above was measured so as to calibrate the conductivity meter. To measure the rate of solubilization of the coated particles of the invention containing various quantities of the coating product, there were added to the surface of the constant volume of water, coated particles containing a constant weight $p$ of the antiperspirant derivative of aluminum, whereby the solubilization curve of the coated product for the various quantities of the coated product employed was easily obtained.

The rate of solubilization is thus determined using a conventional conductivity meter equipped with a recording device to provide the rate of solubilization curve. This test provides a measurement of the percentage of the antiperspirant derivative, for example, solubilized basic aluminum hydrochloride, as a function of time, which thus gives a reliable picture of the phenomenon that occurs when the particles of the product according to the invention, come into contact with perspiration when deposited on the skin.

The following table indicates, comparatively, the percentages of basic aluminum hydrochloride solubilized as a function of time for two examples of products A and B, obtained in accordance with examples A and B set forth below.

| Time Elapsed | 1 hr. | 2 hrs. | 4 hrs. | 6 hrs. | 8 hrs. | 10 hrs. | 25 hrs. |
|---|---|---|---|---|---|---|---|
| B | 45% | 65% | 80% | 92% | 100% | — | — |
| A | 30% | 43% | 56% | 67% | 75% | 80% | 100% |

From this table it can be seen that product B has essentially completely solubilized at the end of 8 hours, while product A is essentially completely solubilized after a period of about 25 hours.

Thus the application of an aerosol formulation containing the present invention can be made for example in the morning, and its antiperspirant effect can last, at least, for the entire duration of a normal day's activity.

The preceding test employed, as the antiperspirant derivative of aluminum, basic aluminum hydrochloride, but it will be noted that essentially similar results are achieved using other derivatives of aluminum and particularly basic aluminum hydrobromide.

One of the important characteristics of the present invention is to provide a control of the rate of solubilization of the antiperspirant product in contact with perspiration by varying the ratio between the respective weights of the antiperspirant derivative of aluminum and the starch coating therefor, and by producing thus on the skin, so as to protect against perspiration, a potential reserve of antiperspirant agent capable of exeriising its activity over a prolonged period.

The present invention also relates to an antiperspirant composition comprising in an appropriate cosmetic vehicle or carrier, the product defined above. The cosmetic vehicle or carrier is one suitable for topical application to human skin.

The expression "cosmetic vehicle" as employed in the present invention includes all the components of the composition other than the active component, which components thus serve as the vehicle for this active product. The term "cosmetic" as employed in the present invention indicates simply that this vehicle must be able to be applied without any deleterious effect on the skin of the user. The components constituting the vehicle of the deodorant or antiperspirant compositions of the present invention are described in well known works on cosmetology and are designated generally by the expression "cosmetic vehicle". See for example Handbook of Cosmetic Science, cited above, page 332, 9th line from the bottom.

the antiperspirant compositions according to the present invention are principally compositions packaged in the form of aerosols which include, in addition to the product coated in accordance with the invention, an aerosol propellant agent. This propellant agent functions to provide within the aerosol container a pressure sufficient to permit progressive release of the contents of the container through the distribution valve of said container.

It is known that propellant agents generally comprise a liquid or liquefied fluorinated hydrocarbon or a mixture thereof such as those sold under the name "FREON". These aerosol propellant agents are well known and are referred to in the present invention as a fluorohydrocarbon aerosol propellant agent. These propellant agents are principally fluoronated derivatives of methane or ethane and the propellants most often utilized are dichlorodifluoromethane (Freon 12), trichlorofluoromethane (Freon 11), and dichlorotetrafluoroethane (Freon 114). In practice there is generally used either a mixture of Freon 11 and 12 or a mixture of Freon 12 and 114.

It is also well known that there can also be used as a propellant agent, $CO_2$ or nitrous oxide under pressure, in combination with a fluorohydrocarbon propellant agent in which the $CO_2$ or nitrous oxide is partially dissolved. Thus there can be employed, for example, as the aerosol propellant agent, Freon 11 and $CO_2$, or Freon 11 and nitrous oxide; see, for instance, Belgium Pat. No. 763,982.

Publications relating to the production of cosmetic compositions, packaged in the form of aerosols, and in particular those employing fluorohydrocarbon propellant agents, include the work of Hibbott, Handbook of Cosmetic Science, Pergamon Press (1963), Chapter XXIV, as well as the references mentioned in this chapter.

The cosmetic compositions in the form of aerosols according to the present invention can contain, for example, other active components and propellant agents, a perfume, a suspension agent to assist the homogeneity of the mixture such as colloidal silica, and an emollient such as isopropyl palmitate or myristate, or a mixture of these various cosmetic adjuvants for aerosols.

The cosmetic vehicle, when the composition is in the form of an aerosol, is then principally constituted by the aerosol propellant agent, and optionally the perfume, emollient and/or suspension agent.

Additionally, the antiperspirant composition in the form of an aerosol according to the present invention can contain a conventional bactericidal deodorant agent such as, for example, Irgason D.P. 300 (2,4,4'-trichloro-2'-hydroxy diphenyl ether).

Bactericidal deodorant agents used in the deodorant compositions are described in the literature such as the Handbook of Cosmetic Science, pages 332-334. One of the most well known deodorant agents is hexachlorophene.

The perfumes useful in the antiperspirant compositions of the present invention are well known and are disclosed, for instance, in the work of Heizka, International Encyclopedia of Aerosol Packaging, Pergamon, Oxford (1965).

Thus, in the antiperspirant compositions of the present invention, there can be employed, for example, perfumes sold under the following names: Colmen 13182 g and Leralia 18770 (Firmenich), Vervia C7 and 20247 (Creat Aromatiques), VIC 8 and F.N. 3083 (IFF) and E1048 (Aromescence).

The compositions of the invention can also be presented in the form of powders called "talcs".

The preparation of these "talcs", and the nature of the cosmetic vehicles used in such compositions, are described for example in the Handbook of Cosmetic Science, cited above, particularly at pages 339-334.

In addition to the active component, these powders can contain a cosmetic vehicle constituted by talc, which is the most abundant component (60-90 weight percent, generally), perfumes and generally at least one of the following components in the form of a suitably ground powder: titanium oxide, zinc oxide, kaolin, colloidal silica, chalk, calcium phosphate, magnesium carbonate, zinc stearate and magnesium stearate.

The coated antiperspirant derivative of this invention can be present in the antiperspirant composition in amounts ranging between 2-8, preferably, between 3-5, weight percent thereof.

In another embodiment of the present invention, the antiperspirant composition comprises, in addition to the product of the invention, a perfume stable in the presence of antiperspirant derivatives of aluminum and an antiperspirant agent other than the product of the present invention so as to provide a composition exhibiting both immediate action and delayed action against perspiration.

In this embodiment a predetermined quantity of micronized antiperspirant derivative of aluminum in the form of crystals, either not coated or coated with degraded starch, which is immediately soluble in perspiration, such as a starch of waxy maize hydrolyzed to a Stormer viscosity of 85, such as that commerically available under the name "AMIOCA" by National Starch Company, or ordinary cornstarch hydrolyzed to a Stormer viscosity of 65, such as that commerically available under the mark "FLUITEX" by National Starch Company or dextrin, can be added to predetermined quantities of the product of the present invention.

The composition using in combination the antiperspirant product of the present invention exhibiting a delayed action with another antiperspirant agent without a delayed effect provides an effective action against perspiration for a time determined as a function of the relative amount of antiperspirant agents with and without the delay effect. While a wide range of relative amounts of these agents can be employed, it has been found advantageous to employ them in a ratio between about 10:1 and 1:1, preferably between 2:1 and 1:1 parts by weight of the product of this invention per part by weight of said another antiperspirant agent exhibiting essentially no or little delayed action.

The following examples illustrate the preparation of products according to the invention as well as their use in antiperspirant aerosol formulations.

EXAMPLE A 100 g of cornstarch containing about 35 weight percent amylose and 65 weight percent amylopectin, previously subjected to acid hydrolysis under pressure in HCl so as to obtain a Stormer viscosity of 65, are suspended in 900 centiliters of distilled water. The suspension is heated with vigorous agitation up to a temperature of 85° C, at which temperature there is observed partial gelling of the starch and an increase in the viscosity of the mixture. 25 g of crystallized basic aluminum hydrochloride are then added, which dissolve instantly.

The resulting solution is maintained at 85° C and is then charged into the feed end of an atomizer drier by means of an intermediate peristaltic pump. The temperature of the air at the inlet of the atomizer drier is maintained at 215° C during the time of atomization, the exit temperature being between 110-115° C.

At the end of the operation, there are recovered from the cyclone of the atomizer drier, 120 g of a fine powder comprising particles having a diameter between 15-40 microns and having the following composition:

| Basic aluminum hydrochloride: | 1 pbw |
|---|---|
| Starch | 4 pbw |

This powder is submitted to the above described test to measure by a conductivity meter its rate of dissolution in water at 37° C and at a pH of 6. The test shows that 43% of the product is solubilized after 2 hours of contact, 75% after 8 hours, and that 25 hours are required for tatal dissolution. EXAMPLE B 100 g of cornstarch sold under the mark "HI-SET" and corresponding to the specifications of the starch used in Example A are suspended in 950 centiliters of distilled water. The suspension is vigorously agitated and progressively brought to a temperature 85° C. At this stage, a partial dissolution of the starch and an increase in viscosity of the mixture occurs.

With continued agitation, 100 g of a 50 weight percent aqueous solution of basic aluminum hydrochloride is added thereto.

The resulting solution, maintained with agitation at a temperature of 85° C, is then dried with atomization under the same conditions as those described in Example A. From the cyclone of the atomizer drier, 142 g of fine powder are recovered. The individual particles of the powder have a diameter between 10-40 microns and have the following composition:

| Basic aluminum hydrochloride | 1 pbw |
|---|---|
| Starch | 2 pbw |

This powder when subjected to the above test to measure its rate of dissolution in 37° C water at a pH of 6 reveals that 45% of the product are solubilized after 1 hour of contact, 65% after 2 hours, 80% after 4 hours with essentially total dissolution occurring in 8 hours.

EXAMPLE C

In accordance with the procedures employed in Example A, 100 g of basic aluminum hydrochloride are coated with 1000 g of a starch containing 35 percent amylose and 65 percent amylopectin, said starch having been submitted to acid hydrolysis up to a Stormer viscosity of 65.

The basic aluminum hydrochloride is added to an aqueous suspension of the starch heated to 85° C.

EXAMPLE D

In accordance with the procedures employed in Example B, 100 g of basic aluminum hydrochloride are coated with 100 g of starch containing 35 percent amylose and 65 percent amylopectin, said starch having been submitted to acid hydrolysis up to a Stormer viscosity of 65.

The basic aluminum hydrochloride is added to an aqueous suspension of the starch heated to 85° C.

EXAMPLE E

In accordance with the procedures employed in Example A, 50 g of basic aluminum hydrochloride are coated with 400 g of starch containing 35 percent amylose and 65 percent amylopectin, said starch having been submitted to acid hydrolysis up to a Stormer viscosity of 65.

The basic aluminum hydrochloride is added to an aqueous suspension of the starch heated to 85° C.

EXAMPLE F

In accordance with the procedures employed in Example B, 100 g of basic aluminum hydrobromide are coated with 200 g of starch containing 35 percent amylose and 65 percent amylopectin, said starch having been submitted to acid hydrolysis up to a Stormer viscosity of 60.

The basic aluminum hydrobromide is added to an aqueous suspension of the starch heated to 85° C.

EXAMPLE G

In accordance with the procedures employed in Example B, 100 g of basic aluminum hydrochloride are coated with 100 g of starch containing 35 percent amylose and 65 percent amylopectin, said starch having been submitted to acid hydrolysis up to a Stormer viscosity of 60.

The basic aluminum hydrochloride is added to an aqueous suspension of starch heated to 85° C.

EXAMPLE H

In accordance with the procedures employed in Example B, 100 g of basic aluminum hydrochloride are coated with 100 g of starch containing 30 percent amylose and 70 percent amylopectin, said starch having been submitted to acid hydrolysis up to a Stormer viscosity of 60.

The basic aluminum hydrochloride is added to an aqueous suspension of the starch heated to 80° C. EXAMPLE I In accordance with the procedures employed in Example A, 75 g of basic aluminum hydrochloride are coated with 300 g of starch containing 30 percent amylose and 70 percent amylopectin, said starch having been submitted to acid hydrolysis up to a Stormer viscosity of 60.

The basic aluminum hydrochloride is added to an aqueous suspension of starch heated to 80° C.

EXAMPLE J

In accordance with the procedures employed in Example B, 50 g of basic aluminum hydrochloride are coated with 100 g of starch containing 40 percent amylose and 60 percent amylopectin, said starch having been submitted to acid hydrolysis up to a Stormer viscosity of 70.

The basic aluminum hydrochoride is added to an aqueous suspension of the starch heated to 90° C.

EXAMPLE K

In accordance with the procedures employed in Example A, 50 g of basic aluminum hydrochloride are coated with 200 g of starch containing 40 percent amylose and 60 percent amylopectin, said starch having been submitted to acid hydrolysis up to a Stormer viscosity of 70.

The basic aluminum hydrochloride is added to an aqueous suspension of the starch heated to 90° C.

EXAMPLE L

In accordance with the procedures employed in Example A, 20 g of basic aluminum hydrochloride are coated with 200 g of starch containing 40 percent amylose and 60 percent amylopectin, said starch having been submitted to acid hydrolysis up to a Stormer viscosity of 70.

the basic aluminum hydrochloride is added to an aqueous suspension of the starch heated to 90° C.

EXAMPLE M

In accordance with the procedures employed in Example A, 100 g of basic aluminum hydrochloride are coated with 400 g of starch containing 40 percent amylose and 60 percent amylopectin, said starch having been submitted to acid hydrolysis up to a Stormer viscosity of 65.

The basic aluminum hydrochloride is added to an aqueous suspension of the starch heated to 85° C.

EXAMPLE N

In accordance with the procedures employed in Example A, 50 g of basic aluminum hydrochloride are coated with 300 g of starch containing 40 percent amylose and 60 percent amylopectin, said starch having been submitted to acid hydrolysis up to a Stormer viscosity of 65.

The basic aluminum hydrochloride is added to an aqueous suspension of the starch heated to 85° C.

EXAMPLE O

In accordance with the procedures employed in Example A, 25 g of basic aluminum hydrobromide are coated with 100 g of starch containing 35 percent amylose and 65 percent amylopectin, said starch having been submitted to acid hydrolysis up to a Stormer viscosity of 65.

The basic aluminum hydrobromide is added to an aqueous suspension of the starch heated to 85° C.

EXAMPLE P

In accordance with the procedures employed in Example B, 100 g of basic aluminum hydrobromide are coated with 200 g of starch containing 35 percent amylose and 65 percent amylopectin, said starch having been submitted to acid hydrolysis up to a Stormer viscosity of 60.

The basic aluminum hydrobromide is added to an aqueous suspension of the starch heated to 85° C.

EXAMPLE Q

In accordance with the procedures employed in Example A, 30 g of basic aluminum hydrobromide are coated with 120 g of starch containing 30 percent amylose and 70 percent amylopectin, said starch having been submitted to acid hydrolysis up to a Stormer viscosity of 60.

The basic aluminum hydrobromide is added to an aqueous suspension of the starch heated to 80° C.

EXAMPLE R

In accordance with the proceudres employed in Example A, 25 g of basic aluminum hydrobromide are coated with 100 g of starch containing 40 percent amylose and 60 percent amylopectin, said starch having been submitted to acid hydrolysis up to a Stormer viscosity of 70.

The basic aluminum hydrobromide is added to an aqueous suspension of the starch heated to 90° C.

All the coated basic aluminum halide antiperspirant agents obtained in accordance with the preceding examples have a sufficiently slow solubility, at a temperature of 37° C, to permit progressive release of the active component for a period up to several hours.

The following non-limiting examples illustrate antiperspirant compositions of the present invention.

EXAMPLE 1

An antiperspirant composition packaged under pressure as an aerosol is prepared by admixing the following components:

| | |
|---|---|
| Basic aluminum hydrochloride coated as in Example B, powder | 4.00 g |
| Colloidal silica (Aerosil 300-Degussa) | 0.30 g |
| Perfume | 0.50 g |
| Isopropyl myristate | 5.20 g |
| Trichlorofluoromethane | 45.00 g |
| Dichlorodifluoromethane | 45.00 g |
| | 100.00 g |

EXAMPLE 2

An antiperspirant composition packaged under pressure as an aerosol is prepared by admixing the following components:

| | |
|---|---|
| Basic aluminum hydrochloride coated as in Example B, powder | 4.00 g |
| Colloidal silica (Aerosil R972-Degussa) | 0.30 g |
| Irgosan DP 300 | 0.10 g |
| Perfume | 0.60 g |
| Isopropyl palmitate | 5.00 g |
| Trichlorofluoromethane | 45.00 g |
| Dichlorodifluoromethane | 45.00 g |
| | 100.00 g |

These two compositions provide antiperspirant activity for about 25 hours, without irritation of the skin. Further no change in the nature of the perfume is observed during prolonged storage of these compositions in aerosol containers.

EXAMPLE 3

An antiperspirant composition packaged under pressure as an aerosol is prepared by admixing the following components:

| | |
|---|---|
| Basic aluminum hydrochloride coated as in Example B, powder | 4.00 g |
| Basic aluminum hydrochloride (not coated) | 2.00 g |
| Colloidal silica (Aerosil 300-Degussa) | 0.30 g |
| Perfume | 0.70 g |
| Isopropyl myristate | 3.00 g |
| Trichlorofluoromethane | 54.00 g |
| Dichlorodifluoromethane | 36.00 g |
| | 100.00 g |

EXAMPLE 4

An antiperspirant composition packaged under pressure as an aerosol is prepared by admixing the following components:

| | |
|---|---|
| Basic aluminum hydrochloride coated as in Example B, powder | 4.00 g |
| Basic aluminum hydrochloride (not coated) | 2.00 g |
| Colloidal silica (Aerosil R972-Degussa) | 0.30 g |
| Absolute ethyl alcohol | 20.00 g |
| Perfume | 0.70 g |
| Isopropyl palmitate | 3.00 g |
| Trichlorofluoromethane | 42.00 g |
| Dichlorodifluoromethane | 28.00 g |
| | 100.00 g |

EXAMPLE 5

An antiperspirant composition packaged under pressure as an aerosol is prepared by admixing the following components:

| | |
|---|---|
| Basic aluminum hydrochloride coated as in Example A, powder | 2.00 g |
| Basic aluminum hydrochloride coated with starch of waxy maize hydrolyzed to a Stormer viscosity of 85 (no delay effect) | 2.00 g |
| Colloidal silica (Aerosil 300-Degussa) | 0.20 g |
| Perfume | 0.60 g |
| Isopropyl myristate | 5.20 g |
| Trichlorofluoromethane | 45.00 g |
| Dichlorodifluoromethane | 45.00 g |
| | 100.00 g |

Example 6

An antiperspirant composition packaged under pressure as an aerosol is prepared by admixing the following components:

| | |
|---|---|
| Basic aluminum hydrochloride coated as in Example A, powder | 2.00 g |
| Basic aluminum hydrochloride coated with ordinary cornstarch hydrolyzed to a Stormer viscosity of 65 (no delay effect) | 2.00 g |
| Colloidal silica (Aerosil R972-Degussa) | 0.30 g |
| Irgosan DP 300 | 0.10 g |
| Perfume | 0.60 g |
| Absolute ethyl alcohol | 20.00 g |
| Isopropyl palmitate | 5.00 g |
| Trichlorofluoromethane | 35.00 g |

-continued

| | |
|---|---|
| Dichlorodifluoromethane | 35.00 g |
| | 100.00 g |

EXAMPLE 7

An antiperspirant composition packaged under pressure in an aerosol container is prepared by admixing the following components:

| | |
|---|---|
| Product of Example L | 8.00 g |
| Isopropyl palmitate | 3.00 g |
| Perfume - Vervia 7C7 (Creat Aromatiques) | 0.50 g |
| Trichlorofluoromethane | 51.25 g |
| Dichlorodifluoromethane | 37.35 g |
| | 100.00 g |

EXAMPLE 8

An antiperspirant composition packaged under pressure in an aerosol container is prepared by admixing the following components:

| | |
|---|---|
| Product of Example N | 5.25 g |
| Isopropyl myristate | 3.50 g |
| Perfume - Colmen 13182g (Firmenich) | 0.40 g |
| Trichlorofluoromethane | 45.00 g |
| Dichlorodifluoromethane | 45.75 g |
| | 100.00 g |

EXAMPLE 9

An antiperspirant composition packaged under pressure in an aerosol container is prepared by admixing the following components:

| | |
|---|---|
| Product of Example M | 5.00 g |
| Colloidal silica | 0.30 g |
| Isopropyl palmitate | 4.20 g |
| Perfume - E1048 (Aromescence) | 0.50 g |
| Trichlorofluoromethane | 90.00 g |

The above mixture is introduced into a 100 cm$^3$ aerosol container and then saturated with nitrous oxide under pressure so as to establish a pressure therein of 4.5 kg/cm$^2$.

Similar antiperspirant compositions are produced by replacing the product of Example M by that of Example I or Q.

EXAMPLE 10

An antiperspirant composition packaged under pressure in an aerosol container is prepared by admixing the following components:

| | |
|---|---|
| Product of Example O | 4.5 g |
| Colloidal silica | 0.4 g |
| Isopropyl myristate | 3.6 g |
| Perfume - VIC 8 (IFF) | 0.5 g |
| Trichlorofluoromethane | 91.00 g |

The above mixture is introduced into a 100 cm$^3$ aerosol container and then saturated with CO$_2$ under pressure so as to establish a pressure therein of 4.5 kg/cm$^2$.

A similar antiperspirant composition is produced by replacing the product of Example O by the product of Example R.

EXAMPLE 11

An antiperspirant composition packaged under pressure in an aerosol container is prepared by admixing the following components:

| | |
|---|---|
| Product of Example F | 3.00 g |
| Isopropyl palmitate | 7.00 g |
| Perfume - E1048 (Aromescence) | 0.50 g |
| Colloidal silica | 0.30 g |
| Dichlortetrafluoroethane | 71.00 g |
| Dichlorodifluoromethane | 68.00 g |

Similar antiperspirant compositions are produced by replacing the product of Example F by that of Example P or Example B.

EXAMPLE 12

An antiperspirant composition packaged under pressure in an aerosol container is prepared by admixing the following components:

| | |
|---|---|
| Product of Example D | 2.60 g |
| Basic aluminum hydrochloride, coated without delay effect | 2.00 g |
| Isopropyl myristate | 4.00 g |
| Colloidal silica | 0.30 g |
| Perfume - F.N. 3083 (IFF) | 0.70 g |
| Trichlorofluoromethane | 42.60 g |
| Dichlorodifluoromethane | 48.00 g |

A similar antiperspirant composition is produced by replacing the product of Example D by that of Example H.

EXAMPLE 13

An antiperspirant composition packaged under pressure in an aerosol container is prepared by admixing the following components:

| | |
|---|---|
| Product of Example A | 4.30 g |
| Isopropyl palmitate | 3.00 g |
| Perfume - Colmen 13182 g (Firmenich) | 0.40 g |
| Colloidal silica | 0.30 g |
| Trichlorofluoromethane | 55.00 g |
| Dichlorodifluoromethane | 37.00 g |

EXAMPLE 14

An antiperspirant composition packaged under pressure in an aerosol container is prepared by admixing the following components:

| | |
|---|---|
| Product of Example G | 2.00 g |
| Colloidal silica | 0.20 g |
| Perfume -E1048 (Aromescence) | 0.30 g |
| Isopropyl myristate | 3.00 g |
| Trichlorofluoromethane | 49.50 g |
| Dichlorodifluoromethane | 45.00 g |

A similar antiperspirant composition is produced by replacing the product of Example G by the product of Example D.

EXAMPLE 15

An antiperspirant composition packaged under pressure in an aerosol container is prepared by admixing the following components:

| | |
|---|---|
| Product of Example B | 3.00 g |
| Isopropyl palmitate | 3.00 g |
| Perfume - Vervia C7 (Creat Aromatiques) | 0.40 g |
| Trichlorofluoromethane | 53.60 g |
| Dichlorodifluoromethane | 40.00 g |

Similar antiperspirant compositions are produced by replacing the product of Example B by the product of Example P or Example J.

EXAMPLE 16

An antiperspirant talc having the following composition is prepared:

| | |
|---|---|
| Talc | 80.00 g |
| Zinc oxide | 4.00 g |
| Magnesium stearate | 6.00 g |
| Colloidal silica | 1.00 g |
| Product of Example E | 8.00 g |
| Perfume | 1.00 g |

A similar antiperspirant talc is produced by replacing the product of Example E by the product of Example L.

EXAMPLE 17

An antiperspirant talc is prepared by mixing and grinding to a powder the following components:

| | |
|---|---|
| Talc | 75.00 g |
| Kaolin | 12.00 g |
| Zinc stearate | 6.00 g |
| Colloidal silica | 1.00 g |
| Perfume | 1.00 g |
| Product of Example A | 5.00 g |

Similar antiperspirant talcs are produced by replacing the product of Example A by the product of Example I or Example Q.

EXAMPLE 18

An antiperspirant talc having the following composition is prepared:

| | |
|---|---|
| Talc | 85.00 g |
| Titanium oxide | 3.00 g |
| Magnesium carbonate | 1.00 g |
| Calcium carbonate (chalk) | 4.00 g |
| Perfume | 1.00 g |
| Product of Example B | 4.00 g |
| Basic aluminum hydrochloride, coated without delay effect | 1.00 g |

Similar antiperspirant talcs are prepared by replacing the product of Example B by the product of Example F, Example J or Example P.

The addition of an antiperspirant agent having an instantaneous effect provides not only instantaneous protection but also good antiperspirant effectiveness over a period of time. These compositions also exhibit excellent stability characteristics during prolonged storage.

What is claimed is:

1. In an antiperspirant agent consisting of coated mircocrystals of basic aluminum hydrohalide, the improvement comprising, as the coating for said basic aluminum hydrohalide, partially degraded, acid hydrolyzed starch having a Stormer viscosity between 60–70, said starch comprising 30–40 weight percent amylose and 60–70 weight percent amylopectin, wherein the weight ratio of said aluminum hydrohalide to said starch (dry basis) is between 1:10 and 1:1, so as to provide a delayed antiperspirant effect.

2. The antiperspirant agent of claim 1, wherein said starch is cornstarch containing 35 weght percent amylose.

3. The antiperspirant agent of claim 1 wherein said aluminum hydrohalide is selected from the group consisting of basic aluminum hydrochloride and basic aluminum hydrobromide.

4. The antiperspirant agent of claim 1, in the form of a powder, the diameter of the particles of the powder ranging between 10–50 microns.

5. A process for preparing the antiperspirant agent of claim 1 comprising introducing into a current of air produced in an atomizer drier an aqueous gel consisting essentially of said partially degraded starch containing in solution said aluminum hydrohalide, said air being at a temperature ranging from 200°–230° C at the inlet of said drier to 110°–120° C at the outlet of said drier, said aqueous gel having a starch concentration between 5–30 percent by weight and the weight ratio of said aluminum hydrohalide to starch (dry basis) being between 1:10 and 1:1.

6. The process of claim 5 wherein said aqueous gel is obtained by producing a suspension of said starch in cold water, heating said suspension with agitation to a temperature between 80°–90° C so as to impart fluidity thereto and adding thereto said aluminum hydrohalide either in crystalline form or in the form of an aqueous solution thereof.

7. The process of claim 5 wherein the concentration of partially degraded starch in the aqueous gel is between 10–15 weight percent thereof.

8. Antiperspirant composition comprising in a cosmetic vehicle suitable for topical application to human skin, the antiperspirant agent of claim 1 in an amount of 2–8 percent by weight of said composition.

9. The antiperspirant composition of claim 8 wherein said cosmetic vehicle comprises an aerosol propellant and said composition is packaged under pressure in an aerosol container.

10. The antiperspirant composition of claim 9 wherein said aerosol propellant is a chlorofluorinated hydrocarbon.

11. The antiperspirant composition of claim 9 wherein said cosmetic vehicle also includes at least one of a deodorizing bactericide, a perfume, a suspension agent and an emollient.

12. The antiperspirant composition of claim 8 wherein said antiperspirant agent is present in an amount of 3–5 percent by weight of said composition.

13. The antiperspirant compositon of claim 8 which also includes another antiperspirant agent.

14. The antiperspirant composition of claim 13 wherein said another antiperspirant agent is micronized non-coated basic aluminum hydrochloride.

15. The antiperspirant composition of claim 13 wherein said another antiperspirant agent is basic aluminum hydrochloride in the form of crystals coated with a starch which rapidly dissolves in water or perspiration.

16. The antiperspirant composition of claim 8 wherein said cosmetic vehicle is a talc.

* * * * *